United States Patent [19]

Osada et al.

[11] Patent Number: 4,653,500
[45] Date of Patent: Mar. 31, 1987

[54] ELECTROCARDIOGRAPHIC AMORPHOUS ALLOY ELECTRODE

[75] Inventors: Soichi Osada, Matudo; Hirokatsu Inoue, Chiba; Chuji Shimizu, Funabashi; Yasuaki Onodera, Saitamaken; Ken-ichi Kobayashi, Gunma; Kazuo Kozima, Abiko; Shigeyoshi Shioda, Kamagaya, all of Japan

[73] Assignees: Fukuda Denshi Co., Ltd.; Japan Metals & Chemicals Co., Ltd., both of Tokyo, Japan

[21] Appl. No.: 809,967

[22] Filed: Dec. 17, 1985

[30] Foreign Application Priority Data

Jun. 18, 1985 [JP] Japan ................................ 60-130775

[51] Int. Cl.$^4$ .............................................. A61B 5/04
[52] U.S. Cl. ..................................... 128/639; 128/644; 252/503; 252/513
[58] Field of Search ................................ 128/639–644, 128/783–786, 419 P, 802, 803, 798; 252/503, 513, 519

[56] References Cited

U.S. PATENT DOCUMENTS 4,287,896  9/1981  Grigorov ........................... 128/786
4,448,199  5/1984  Schmid ............................. 128/639

FOREIGN PATENT DOCUMENTS 0022556  1/1981  European Pat. Off. ............ 128/784

OTHER PUBLICATIONS

Stuyck et al., "A Suitable . . . Electrodes", Ellectromyogr Clin Neuro, 1975, No. 3, 15, 291.

Primary Examiner—Lee S. Cohen
Attorney, Agent, or Firm—Pollock, VandeSande & Priddy

[57] ABSTRACT

An electrocardiographic amorphous alloy electrode is manufactured from an iron-based (or nickel-based) amorphous alloy containing chromium as a metallic element and also containing at least one member of a group consisting of phosphorus, carbon, silicon and boron as a non-metallic element or semi-metallic elements.

6 Claims, 3 Drawing Figures

ELECTROCARDIOGRAPHIC AMORPHOUS ALLOY ELECTRODE

FIELD OF THE INVENTION

This invention relates to an electrocardiographic amorphous alloy electrode to be applied to a living body for obtaining an electrocardiogram and, more particularly, to an electrocardiographic amorphous alloy electrode of the type noted, which has excellent corrosion resistance and can be manufactured at a low cost.

PRIOR ART

As is well known in the art, bioelectricity is included in the living body by the activities of the heart, muscles, etc.

Particularly, bioelectricity of the heart is used for the diagnosis of the heart by leading a weak current induced on man's skin surface to an external electrocardiogram. In the electrocardiograph, electrodes are essential components which are held in contact with the skin surface to electrically couple the living body to an input section of the electrocardiograph.

The electrodes are important components for accurately measuring the bioelectric potential with high accuracy and realizing a high waveform discrimination ratio.

This important electrode must satisfy three requirements, i.e., low electrical resistance, excellent corrosion resistance and chemical stability.

More specifically, the electrode should have low electric resistance, that is, it should be a good electric conductor, in order to be able to lead even a very weak electric current in a living body to the outside thereof.

Besides, since the electrode is used in medical institutions, it is often in contact with various chemicals and very liable to be attacked by these chemicals. Therefore, it should have excellent corrosion resistance.

Further, the electrode may undergo a chemical change when it is brought into contact with a living body. Such a chemical change will induce an electromotive force or a so-called polarization voltage. The polarization voltage is superimposed on the input signal (i.e., electrocardiographic signal) to the electrocardiogram and has adverse effects on an input amplifier of the electrocardiograph. The higher this voltage, the more undesirable it is from the standpoint of the accuracy of electrocardiography. Therefore, the electrode is required to be chemically stable.

Materials that possess the electrical properties as noted above are alloys of silver and silver chloride, and these alloys have heretofore been used extensively for the electrocardiographic electrode.

The alloys containing silver are best suited for the electrocardiographic electrode because they have high conductivity and excellent corrosion resistance and are chemically stable. However, silver is expensive and is produced in small quantities so that it is not so readily available. For this reason, an electrocardiographic electrode material has been desired, which is inexpensive, has excellent corrosion resistance and is readily available.

SUMMARY OF THE INVENTION

The invention has been made in light of the above problems, and its object is to provide an electrocardiographic amorphous alloy electrode, which has excellent corrosion resistance and can be manufactured inexpensively.

According to the invention, there is provided an electrocardiographic amorphous alloy electrode consisting of an iron-chromium system amorphous alloy composed of iron and chromium as metallic elements and also containing a non-metallic element, wherein chromium is contained in 1 to 35 atomic %, the non-metallic element being at least one member of a group consisting of phosphorus, carbon, silicon and boron and contained in a concentration of from about 10 to 25 atomic %.

DETAILED DESCRIPTION OF THE INVENTION

Figure 1:
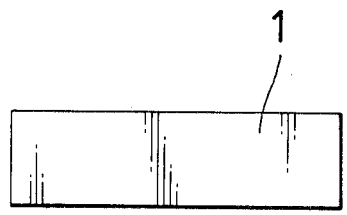
FIG. 1 is a plan view showing an electrocardiographic amorphous alloy electrode embodying the invention.

Among the prior art, extensively used corrosion-resistant alloys are stainless steel alloys, e.g., 13-% chromium steel, 18-8 stainless steel (304 steel), 17-14-25 molybdenum stainless steel, and nickel alloys. These alloys have certain degrees of corrosion resistance. However, under a highly corrosive condition, e.g., 1-N hydrochloric acid aqueous solution, their passive state film is broken so that they are corroded.

Accordingly, the inventors have conducted research and investigations concerning amorphous alloys to find chromium-containing iron-based amorphous alloys which have excellent corrosion resistance and iron-based amorphous alloys which are obtained by adding molybdenum as an auxiliary component to the chromium-containing iron-based amorphous alloys noted above.

The reasons for incorporating the metallic elements noted above into the iron-based amorphous alloys and their ranges will now be described.

As is well known in the art, an amorphous alloy usually is more likely to be corroded than the crystaline alloy of the same composition because of its higher activities. Chromium-containing iron-based amorphous alloys, however, have higher corrosion resistance than crystalline alloys of the same composition and prior art corrosion-resistant alloys. Further, the corrosion resistance of a chromium-containing iron-based amorphous alloy is improved by adding molybdenum.

The inventors have studied to determine why the chromium-containing iron-based alloy has the high corrosion resistance, and they have found that the high corrosion resistance is due to the chemical uniformity and high activity of the amorphous alloy itself, the chemical uniformity being effective for the formation of a uniform passive state film and the high activity being effective for quick formation of a firm and dense passive state film. The passive state film mainly consists of a hydrate of a hydroxide of chromium, and enrichment of the chromium hydroxide in the passive state film is very important for the high degree protective properties of the passive state film. Molybdenum is highly effective for the enrichment of the chromium hydroxide in the passive state film. Therefore, the addition of chromium is indispensable for the corrosion resistance, and the addition of molybdenum promotes the formation of the passive state film.

The compositions, with which a sufficient passive state can be obtained, will now be described.

In the chromium-containing iron-based amorphous alloy, a chromium content of 1 atomic % or above is necessary for sufficient passive state to be ensured so that the alloy is corrosion-resistant under a corrosive condition of a 1-mole saline solution. When the chromium content is increased, the corrosion resistance is obtained under a proportionally increased corrosive condition. When the chromium content is increased beyond 35 atomic %, however, the amorphous state formation capacity is increased. Accordingly, the chromium content range, which ensures the corrosion resistance necessary for the electrocardiographic electrode and permits ready manufacture of an amorphous alloy, is set to 1 to 35 atomic %.

The addition of molybdenum as a metallic element to the chromium-containing iron-based amorphous alloy has an effect of promoting the growth of the passive state film so that a higher corrosion resistance can be obtained. For example, in an iron-based amorphous alloy containing chromium and molybdenum and also containing 13 atomic % of phosphorus and 7 atomic % of carbon as non-metallic elements, a sufficiently passive state is obtained by the addition of 5 atomic % of molybdenum with a chromium content of 10 atomic % or above, and by the addition of 10 atomic % of molybdenum with a chromium content of 5 atomic % or above at room temperature and with a 6-N hydrochloric acid aqueous solution. That is, even under a very strong corrosive condition such as the 6-N hydrochloric acid aqueous solution, the corrosion resistance can be obtained with a chromium content of 5 atomic % or above and with the content of the sum of chromium and molybdenum of 15 atomic % or above. By increasing the chromium content, the necessary molybdenum content is reduced because of the formation of satisfactory passive state. Further, although the addition of a large quantity of molybdenum has an effect of increasing the corrosion potential, the corrosion speed is fixed when the molybdenum exceeds a predetermined amount. Therefore, increasing the molybdenum content beyond 20 atomic % is not advisable because molybdenum is an expensive element. When the molybdenum content exceeds 20 atomic % or when the content of the sum of chromium and molybdenum exceeds 35%, the amorphous state formation capacity is deteriorated.

Now, non-metallic elements to be selected and their content will be described.

For the manufacture of an amorphous alloy, it is necessary to add non-metallic elements. As the non-metallic elements, phosphorus, carbon, boron, silicon and germanium are used, and these semi-metallic elements provide for different features or characteristics of the resultant amorphous alloys. Of these elements germanium provides for inferior corrosion resistance and also leads to high material cost. For this reason, at least one member of a group consisting of phosphorus, carbon, silicon and boron is used in a concentration of about 10 to 25 atomic %.

The chromium-containing iron amorphous alloys, where the non-metallic elements as noted above are incorporated, have characteristics to be described. Alloys containing phosphorus are most satisfactory so far as the corrosion resistance is concerned. Where one phosphorus is used, however, the amorphous state formation capacity is slightly inferior.

Where only carbon is used, the amorphous state formation capacity is slightly inferior, as in the case of phosphorus is the sole non-metallic element, although the corrosion resistance is satisfactory. The amorphous state formation capacity of these alloys, however, can be readily improved by using two or more different non-metallic elements in combination. For example, where phosphorus and carbon are used in combination, satisfactory corrosion resistance can be obtained, and also the amorphous state formation capacity is satisfactory. Alloys containing boron or silicon are inferior in the corrosion resistance to those containing phosphorus and carbon. This, however, poses no particular problem where the alloys are used for the electrocardiographic electrode. Alloys containing boron as the non-metallic element are particularly superior in the amorphous state formation capacity. In view of the price and availability, carbon, phosphorus and silicon are inexpensively and readily available, and boron is most expensive. In the actual manufacture, it is advisable to take the above various characteristics into consideration to select the best system; suitable systems are phosphorus-carbon systems, phosphorus-silicon systems, phosphorus-boron systems and carbon-boron systems.

The contents of these non-metallic elements will now be described. Where the content of the non-metallic elements is less than 10 atomic %, the formation of an amorphous alloy is difficult. Increasing the content of non-metallic elements has an effect of improving the corrosion resistance. Therefore, increasing the content of the non-metallic elements to provide for the same corrosion resistance permits the saving of chromium and molybdenum as the metallic elements. This is economically very important for actual alloys because chromium and molybdenum are comparatively expensive metalic elements. Where the content of the sum of non-metalic elements exceeds 25 atomic %, the amorphous state formation capacity of alloy is deteriorated. Therefore, the content of the non-metallic elements should not exceed 25 atomic % or above.

The iron-chromium system amorphous alloy, according to the invention, may be manufactured by the ordinary liquid metal superquick cooling process. Regarding the components of the alloy composition, pig iron or pure iron is used for the iron source. For chromium or molybdenum as metallic elements, either commercially available pure metal or ferrochromium or ferromolybdenum is used. For the non-metallic element source either commercially available pure materials or ferroboron, ferrophosphorus, ferrosilicon or cementite is used. After the composition has been prepared, it is melted by heating, and the molten material is injected through a nozzle onto a moving cooling surface of a cooling body to be quickly cooled down and solidified to obtain the alloy according to the invention. Alternatively, the molten material may be injected into a cool medium such as water to quickly cooling down and solidifying it.

The fact that ferroalloys may be used as alloy element sources for the alloy according to the invention make the invention advantageous from the standpoints of economy and productivity. More specifically, ferrochromium and ferromolybdenum are the most inexpensive materials up to date as the sources of chromium or molybdenum. Further, ferrochromium has a low melting point, and ferromolybdenum has a very low melting point compared to pure molybdenum so that it is suitable for mass production of homogeneous melted alloy. Further, inpurities in these ferroalloys are mainly phosphorus, carbon and silicon, which are necessary elements for the manufacture of the alloy according to the invention. Further, the amorphous alloy according to the invention may be manufactured as fine strips or thin sheets.

Figure 2:
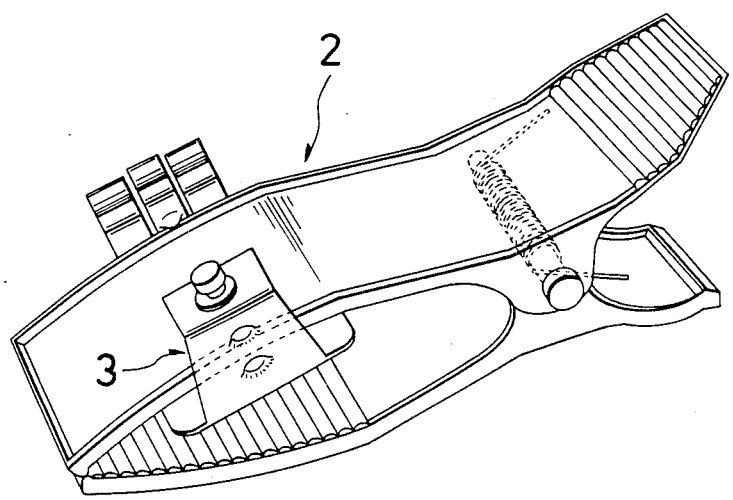
FIGS. 2 and 3 are respectively a perspective view and a pictorial perspective view illustrating the manner in which the electrode according to the invention is used.

The figures of the accompanying drawings illustrate the manner in which the electrode consisting of the amorphous alloy prepared in the above method is used. FIG. 1 is a plan view of the electrocardiographic electrode 1 which is formed as a fine strip or thin sheet of the amorphous alloy. As shown in FIG. 2, this amorphous alloy is used as an electrode section 3 of the chip type electrode 2, the amorphous alloy electrode section 3 being coupled to the clip type electrode 2.

Figure 3:
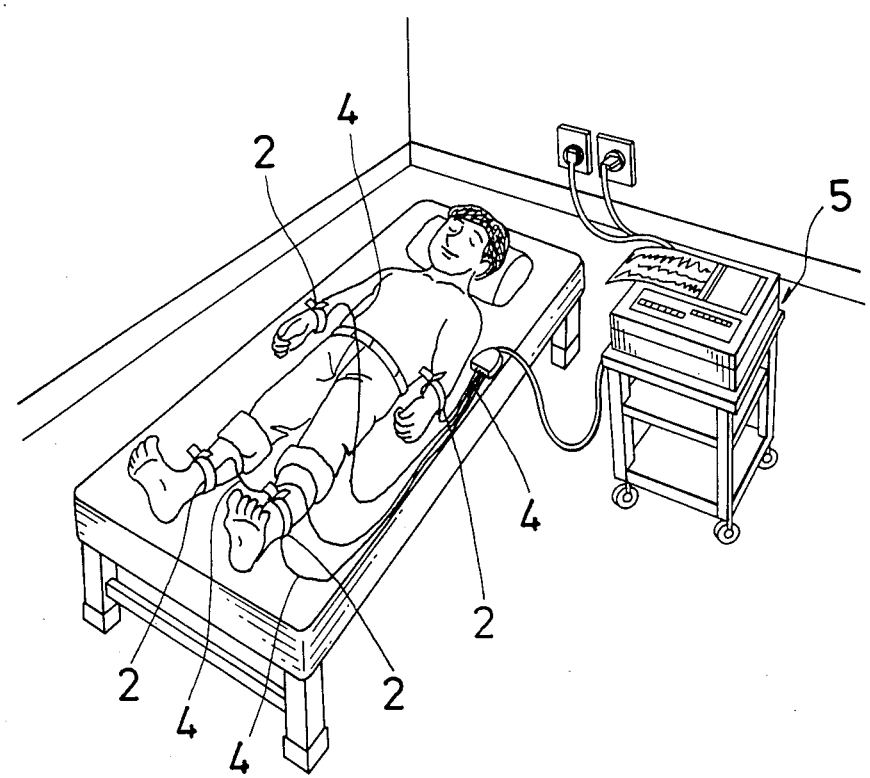

As shown in FIG. 3, such clip type electrodes 2 are applied to the patient's arms and legs, whereby a weak current induced on the patient's skin surface is led through cords 4 to an electrocardiogram 5 to obtain an electrocardiograph.

EFFECTIVENESS OF THE INVENTION

As has been described in the foregoing, the electrocardiographic amorphous alloy electrode according to the invention consists of an amorphous alloy based on iron, so that it can be inexpensively manufactured. In addition, the amorphous alloy electrode has excellent corrosion resistance and long life. Further, the amorphous alloy electrode is chemically stable. Furthermore, since it is in the form of a fine strip or thin sheet, it can be easily bent to fit the irregular configuration of the skin surface, which is desired as the electrocardiographic electrode.

What is claimed is:

1. An electrocardiographic electrode consisting of an iron-based amorphous alloy containing iron, chromium and molybdenum as metallic elements and at least one non-metallic element selected from the group consisting of phosphorus, carbon, silicon and boron, the content of molybdenum being less than 20 atomic percent, and the sum of the concentrations of molybdenum and chromium being from about 1 to about 35 atomic percent.

2. An electrocardiographic electrode according to claim 1 wherein said non-metallic element comprises phosphorus.

3. An electrocardiographic electrode according to claim 1 containing at least one member of the group consisting of phosphorus-carbon, phosphorus-silicon, phosphorus-boron and carbon-boron.

4. An electrocardiographic electrode according to claim 1 wherein said non-metallic element is present in a concentration from about 10 to about 25 atomic percent.

5. An electrocardiographic electrode according to claim 1 wherein the concentration of molybdenum is at least about 5 atomic percent, the concentration of chromium is at least about 10 atomic percent, and the remainder of the metallic elements is iron.

6. An electrocardiographic electrode according to claim 1 wherein the concentration of molybdenum is at least about 10 atomic percent, the concentration of chromium is at least about 5 atomic percent and the remainder of the metallic elements is iron.

* * * * *

UNITED STATES PATENT AND TRADEMARK OFFICE
CERTIFICATE OF CORRECTION

PATENT NO. : 4,653,500
DATED : March 31, 1987
INVENTOR(S) : Soichi Osada, et al.

It is certified that error appears in the above—identified patent and that said Letters Patent is hereby corrected as shown below:

Column 2, line 46, change "crystaline" to --crystalline--;

Column 3, line 56, change "semi-metallic" to --non-metallic--;

Column 3, line 68, change "one" to --only--;

Column 4, line 38, change "metalic" to --metallic--;

Column 4, line 39, change "non-metalic" to --non-metallic--;

Column 4, line 42, delete "or above";

Column 4, line 58, change "cool" to --cooling--;

Column 4, line 59, change "cooling" to --cool-- and change "solidifying" to --solidify--;

Column 5, line 3, change "inpurities" to --impurities--;

UNITED STATES PATENT AND TRADEMARK OFFICE
CERTIFICATE OF CORRECTION

PATENT NO. : 4,653,500

DATED : March 31, 1987

INVENTOR(S) : Soichi Osada, et al

It is certified that error appears in the above-identified patent and that said Letters Patent is hereby corrected as shown below:

Column 5, line 15, change "chip' to -- clip --.

Signed and Sealed this

Twenty-ninth Day of September, 1987

Attest:

DONALD J. QUIGG

*Attesting Officer*   *Commissioner of Patents and Trademarks*